United States Patent [19]
Tu et al.

[11] Patent Number: 5,843,152
[45] Date of Patent: Dec. 1, 1998

[54] CATHETER SYSTEM HAVING A BALL ELECTRODE

[75] Inventors: Hosheng Tu, Tustin; Weng-Kwen Raymond Chia, Irvine, both of Calif.

[73] Assignee: Irvine Biomedical, Inc., Irvine, Calif.

[21] Appl. No.: 867,469

[22] Filed: Jun. 2, 1997

[51] Int. Cl.⁶ ........................................................ A61N 1/06
[52] U.S. Cl. ............................................. 607/122; 606/41
[58] Field of Search ........................ 606/29, 41; 607/119, 607/125, 121, 154, 122

[56] References Cited

U.S. PATENT DOCUMENTS

| | | | |
|---|---|---|---|
| 5,242,441 | 9/1993 | Avitall | 606/41 |
| 5,282,844 | 2/1994 | Stokes et al. | 607/120 |
| 5,643,255 | 7/1997 | Organ | 606/41 |

*Primary Examiner*—Scott M. Getzow

[57] ABSTRACT

An improved catheter system having at least one electrode at its tip section, can be used in ablating the arrhythmogenic point of a patient. A catheter suitable for radiofrequency ablation of cardiac tissues comprises a catheter shaft having a distal section, a distal end, a proximal end and at least one lumen extending therebetween, wherein a rotatable ball electrode is disposed at the tip section of said catheter. In one embodiment, the ablation catheter has a temperature sensor and a close-loop temperature control mechanism. In another embodiment, the ablation catheter has fluid infusion and irrigation means at its distal tip section for creating a deep and large lesion by applying radiofrequency energy and cooled fluid to said electrode.

20 Claims, 4 Drawing Sheets

CATHETER SYSTEM HAVING A BALL ELECTRODE

FIELD OF THE INVENTION

The present invention generally relates to improved constructions for a catheter system. More particularly, this invention relates to catheters and methods for ablating cardiac tissues via a steerable ablation catheter having a ball electrode at its tip section with fluid infusion and irrigation capabilities for ablating intracardiac tissues resulting in a deeper and larger lesion in the cardiac tissue of the heart.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart. The heart includes a number of normal pathways which are responsible for the propagation of electrical signals from upper to lower chamber necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols which have proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in Iorder to ablate the tissue of arrhythmogenic site or the accessory pathway. By successfully destroying that tissue, the abnormal signal patterns responsible for the tachycardia may be eliminated.

The impedance usually rises at the tissue contact site when RF energy is delivered through an electrode. To create a deeper and larger lesion, the surface of the tissue contact sites needs to maintain a proper temperature by a cooled fluid irrigation or infusion to partially compensate for the temperature rise due to RF energy delivery. The following U.S. patents have disclosed use of irrigation ports in different manners to cool the tissue contact surface. Those patents are U.S. Pat No. 5,545,161 to Imran, U.S. Pat. No. 5,462,521 to Brucker et al., U.S. Pat. No. 5,437,662 to Nardella, U.S. Pat. No. 5,423,811 to Imran et al., U.S. Pat. No. 5,348,554 to Imran et al., and U.S. Pat No. 5,334,193 to Nardelia. In practice, the fluid coming out of the irrigation ports may not evenly cover all the surface area of the electrode or the tissue to be ablated. Furthermore, none of the above discloses an irrigation system of cooled fluid through a rotatable electrode means to form a uniform protective fluid layer around the electrode.

The tip section of a catheter is referred to herein as the portion of that catheter shaft containing at least one electrode. In one embodiment, a catheter utilized in the endocardial radiofrequency ablation is inserted into a major vein or artery, usually in the neck or groin area. The catheter is then guided into an appropriate chamber of the heart by appropriate manipulation through the vein or artery. The tip of a catheter must be manipulatable by a physician from the proximal end of the catheter, so that the electrodes at the tip section can be positioned against the tissue site to be ablated. The catheter must have a great deal of flexibility in order to follow the pathway of major blood vessels into the heart. It must permit user manipulation of the tip even when the catheter body is in a curved and/or twisted configuration.

The tip section of a conventional electrophysiology catheter that is deflectable usually contains one large electrode about 4 mm in length for ablation purpose. The lesion is generally not deep because of potential impedance rise of the tissue in contact with the "stationary" catheter electrode and thereafter the ablation time needs to be cut short. The word "stationary" means that the contact point of the electrode with the tissue is the same point unless the electrode is rotatable so that the contact point changes from time to time. In some cases, the contact of a stationary electrode of the conventional catheter with tissues reportedly results in potential tissue adhering to said electrode. A rotatable electrode is in need to reduce the tissue contact impedance rise and temperature rise by slightly moving the rotatable electrode around in a micro-moving manner so that the temperature rise is decreased by the surrounding fluid or by the irrigation fluid. Even in the case of a conventional catheter having irrigation capabilities by utilizing an irrigation port, the cooled fluid does not evenly and uniformly rinse the electrode, because the electrode is not rotatable.

After the exact location of a target tissue is identified, the ablation catheter may still not easily approach the target site even with assistance of an internal viewing means. This viewing situation may turn into a nightmare when an internal viewing approach becomes prohibitive or unavailable during procedures. An external ultrasonic imaging capability therefore becomes in need so that ablation is not taking place in an inappropriate location. The fluoroscope time can be substantially cut short when an external ultrasonic imaging is used instead. In the U.S. Pat. No. 4,794,931, there has been disclosed a catheter and system which can be utilized for ultrasonic imaging. However, there is no disclosure to how such a catheter and system can be utilized in conjunction with an endocardial or epicardial ablation catheter having a rotatable electrode with irrigation capabilities to achieve the desired ultrasonic imaging and ultimately the desired ablation.

Avitall in the U.S. Pat No. 5,242,441, teaches a rotatable tip electrode. Said electrode is secured to a high torque wire for rotation and electrical conductivity. The tissue contact site is always the same spot even the electrode is rotated. The potential coagulum at the contact spot due to impedance rise, would not go away because of its relatively stationary position of the rotatable tip electrode and absence of fluid irrigation.

While a radiofrequency electrophysiology ablation procedure using an existing catheter has had promising results, the tip section of a known catheter usually has a fixed non-rotatable electrode and a fluid infusion port which may not evenly rinse the electrode when contacting the tissue for ablation purpose. Therefore there is a need for an improved catheter and methods for making a deeper and larger lesion in the cardiac tissue.

SUMMARY OF THE INVENTION

In general, it is an object of the present invention to provide an improved catheter for even fluid infusion and irrigation. This capability of even fluid infusion may be applicable to the drug delivery means for treating tumors or cancers. The capability of even fluid irrigation may be applicable to special means of cooling off the tissue contact site due to impedance rise as a result of ablation operation. It is another object of the invention to provide an ablation catheter with a tip section having a ball electrode. It is another object of the invention to provide a free rotatable ball electrode to be used in effectively ablating the arrhythmogenic point of a patient. This catheter is particularly useful for treating the patient with tachycardia as a result of its cooled electrode by applying fluid irrigation means. The fluid may be selected from the group of saline, heparin, antibiotics, chemotherapy and therapeutics fluids.

In one embodiment, an ablation catheter system comprises a catheter shaft having a distal tip section, a distal end, a proximal end and at least one lumen extending therebetween. A handle is attached to the proximal end of said catheter shaft. A distal tip section of the catheter shaft which is proximal to the distal end, comprises a hollow pocket having a ball electrode inside it, and a lumen having fluid infusion and irrigation capabilities. In another embodiment, the ball of the ball electrode is free to float, roll, or rotate within the pocket, wherein the shape of the ball is not limited to the round shape.

A fluid source is positioned at one end of the catheter for supplying a fluid flow through the lumen of said catheter shaft to the tip section which has a ball electrode. Therefore at ablation time, the tip section with a ball electrode is positioned against the tissues to be ablated. The fluid is continuously or intermittently supplied through the lumen to evenly cover and rinse the electrode so that the impedance rise at the contact site is substantially reduced. Cooling off the electrode during RF energy delivery will result in optimal ablation efficiency and a desired deep and large lesion.

In a further embodiment, the catheter comprises a flat wire which is disposed inside the lumen of the catheter shaft. The proximal end of said flat wire is secured to a deployment means on the handle of said catheter system, and is further connected to a conducting wire which is soldered to a contact pin of the connector which is secured at the proximal end of the handle. Therefrom, the conducting wire is connected to an external RF generator for ablation operations using the ball electrode and/or to an EKG monitor for recording and displaying of the endocardial electrical signal.

The distal end of the flat wire is shaped as a receptive concave bowl. The concave bowl comprises an appropriate radius as that of the bail, and contacts the surface of the ball appropriately when the ball is pressed inwardly during contacting the tissue. In an alternate embodiment, the distal end of the flat wire is equipped with a brush-like pick off mechanism for the ball to intimately contact the flat wire when the deployment means is deployed. The contact of the flat wire with the ball constitutes the ball electrode for mapping and/or ablation purpose. A flat wire deployment means on the handle can be deployed so that the flat wire is pushed forward and the ball electrode is forced to tightly position itself against the tip of the catheter shaft, wherein the tip is bent slightly inward to hold the ball in the hollow pocket. When the ball contacts the flat wire to form a ball electrode, the ball electrode can be used as a mapping electrode for recording and displaying the endocardial electrical signal with assistance of an external EKG monitor, and as an ablation electrode in association with an external RF generator energy source. By intermittently contacting the flat wire to the ball, the contacting site of the ball can be rotated and/or the fluid irrigation to the ball electrode can be applied.

The ablation catheter further comprises a steering mechanism at the handle for controlling the deflection of said distal tip section having fluid infusion and irrigation capabilities. Usually a rotating ring or a push-pull plunger is employed in the steering mechanism. In another embodiment, the steerable ablation catheter comprises a bi-directional deflection or multiple curves deflection of the tip section. One end of the steering wire is attached at certain point of the tip section of said catheter shaft. The other end is attached to the steering mechanism at the handle. The steering mechanism on a steerable catheter or device is well-known to those who are skilled in the art.

A fluid conveying lumen is associated the elongate catheter shaft, and is preferably disposed within the catheter shaft along the longitudinal axis thereof. The lumen is adapted to communicate with a fluid supply source to convey fluid from the source and through the lumen to be discharged out of the tip section containing a ball electrode.

The invention also comprises a method and system for controlling the flow rate of fluid through the lumen to optimize the cooling effect of the energy delivering electrode of the catheter. The control system preferably regulates the flow rate based on signals representative of the temperature of the catheter tip and/or tissue impedance.

In a particular embodiment, at least one other electrode is disposed at the tip section of the catheter shaft. One conducting wire which is soldered to said electrode passes through the lumen of the catheter shaft and the interior void of the handle and is thereafter soldered to a contact pin of the connector secured at the proximal end of the handle. Therefrom, the conducting wire is connected to an external RF generator for ablation operations and/or to an EKG monitor for recording and displaying of the endocardial or epicardial electrical signal.

In an additional embodiment, the ablation system further comprises a temperature sensing and close-loop temperature control mechanism for the electrode having at least one temperature sensor at the tissue contact site of the electrode. The location of the temperature sensor is preferably in the very proximity of one of the electrodes. In a still further embodiment, a method for operating an ablation catheter further comprises a programmed temperature control mechanism for independently controlling the delivery of RF energy of each electrode of the ablation catheter.

It is another object of the invention to provide a catheter system with a ball electrode at the side of the tip section of a catheter shaft, instead of at the distal end of said catheter shaft. In one embodiment, said catheter system with side ball electrode comprises fluid irrigation capabilities. In another particular embodiment, the material for the electrodes may consist of conductive metals such as platinum, iridium, gold, silver, stainless steel, Nitinol, or an alloy of their mixture.

A method for operating a steerable ablation catheter system having a ball electrode at the tip section having fluid irrigation means, within a heart chamber comprises: percutaneously introducing the catheter system through a blood vessel to the heart chamber; deflecting the distal section of the catheter about a transverse axis to position the tip section with a ball electrode near a target region on an interior wall of the heart chamber; intimately contacting the electrode with the intracardiac tissue; applying radiofrequency energy to the target location through the electrode; and cooling the electrodes by releasing cooled fluid through the lumen at said distal tip section.

Another object of the invention is to provide a catheter and methods in which it is possible to view the area to be ablated prior to ablation to ensure that ablation is being carried out in an appropriate location. The tip section having a ball electrode is encoded with at least one marker which is visible to ultrasonic energy. The marker has been provided in the form of encapsulated air bubbles.

The catheter system of the present invention has several significant advantages over known catheters or ablation techniques. In particular, the evenly cooled, rotatable ball electrode of a steerable ablation catheter of this invention may result in a deeper and larger lesion which is highly desirable in the tachycardia treatment.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
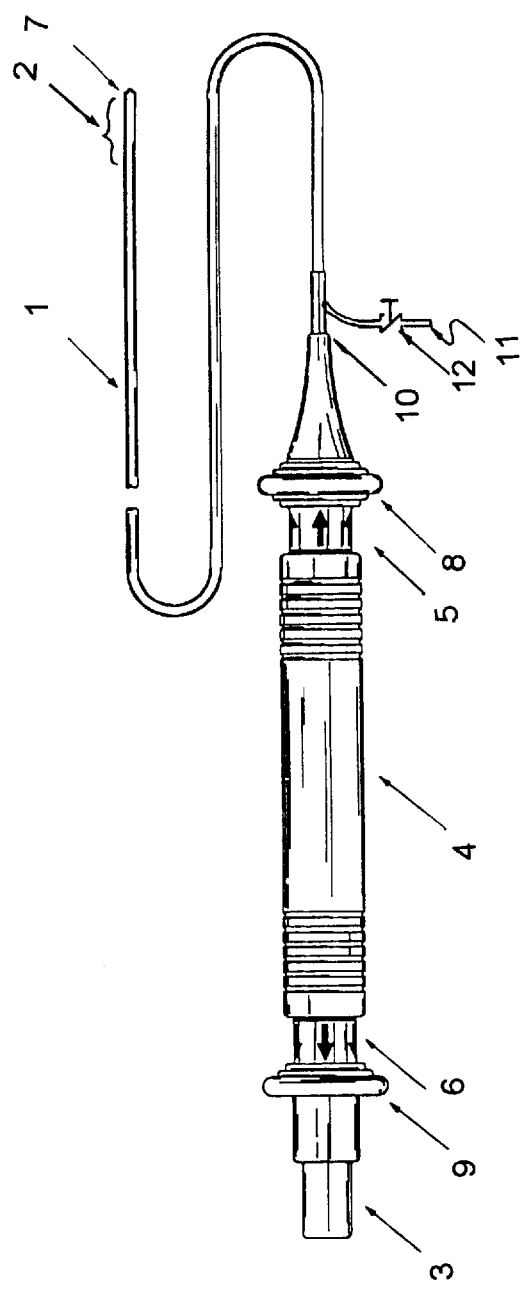
FIG. 1 is an overall view of a catheter system having a ball electrode at its distal tip section constructed in accordance with the principles of the present invention.

FIG. 1 shows an overall view of the catheter system having a ball electrode and fluid infusion and irrigation means. A catheter system constructed in accordance with the principles of the present invention comprises: a catheter shaft 1 having a distal tip section 2, a distal end 7, a proximal end 10, and at least one lumen extending therebetween. The catheter system comprises a fluid infusion mechanism 11 close to the proximal end 10 of the catheter shaft 1. A control valve 12 is provided to the fluid infusion mechanism 11 which is externally connected to a fluid supply source having a pump and means (not shown) for controlling the flow rate of fluid through the lumen to optimize the cooling of the electrode of the catheter. A handle 4 is attached to the proximal end 10 of said catheter shaft 1.

The connector 3 secured at the proximal end of the catheter system, is part of the handle section 4. The handle has one steering mechanism 5. The steering mechanism 5 is to deflect the tip section 2 of the catheter shaft 1 for catheter maneuvering and positioning. By pushing forward the front plunger 8 of the handle 4, the tip section of the catheter shaft deflects to one direction. By pulling back the front plunger 8, the tip section returns to its neutral position. In another embodiment, the steering mechanism 5 at the handle 4 comprises means for providing a plurality of deflectable curves on the distal tip section 2 of the catheter shaft.

Figure 2:
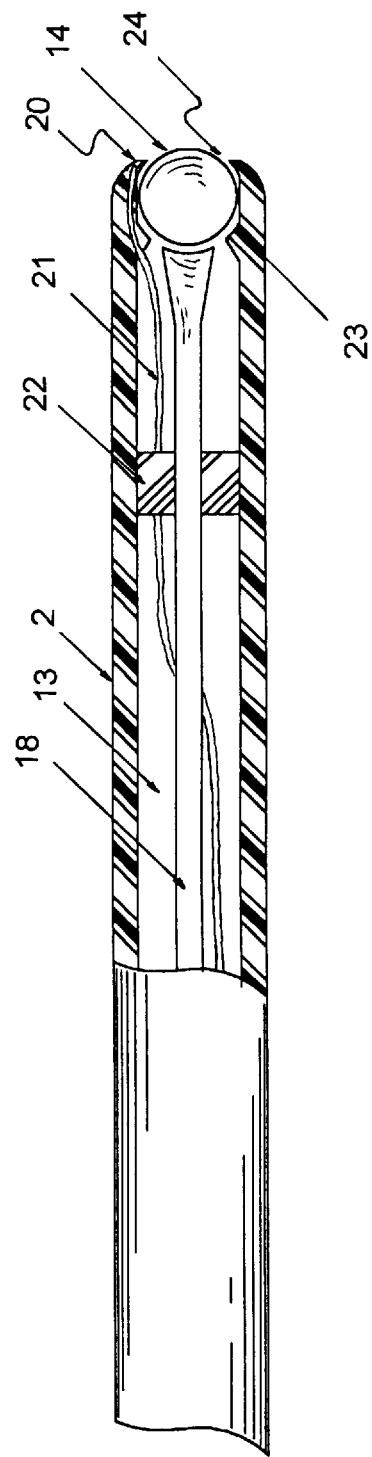
FIG. 2 is a close-up view of the distal section of the catheter system comprising a ball electrode at the distal end having fluid infusion and irrigation capabilities.

FIG. 2 shows a close-up view of the distal section of the catheter system comprising a ball electrode at the distal end having fluid infusion and irrigation capabilities. In one embodiment, a fluid conveying lumen 13 is associated with the elongate catheter shaft 1, and is preferably disposed within the catheter shaft along the longitudinal axis thereof. The fluid conveying lumen is adapted to communicate with a fluid supply source (not shown) to convey fluid from the source and through said lumen to be discharged out of the tip section 2 containing a ball electrode 14 and an opening 24.

Figure 3:
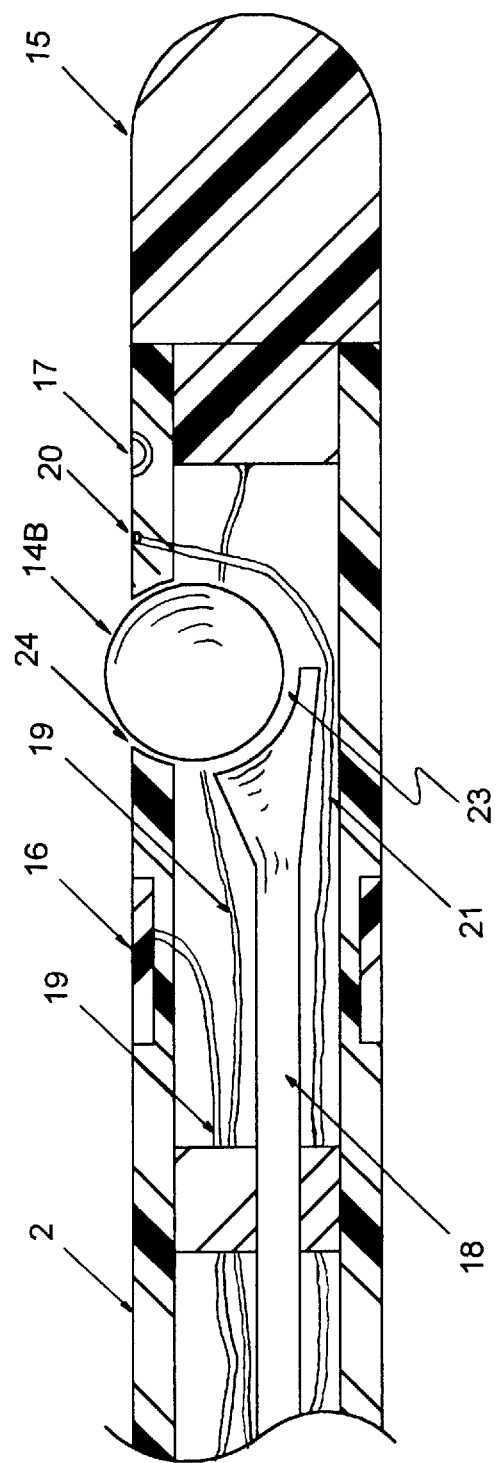
FIG. 3 is a close-up view of the distal section of an alternate catheter system comprising a ball electrode at one side of the tip section having fluid infusion and irrigation capabilities.

FIG. 3 shows a close-up view of the distal section of an alternate catheter system comprising a ball electrode 14B at one side of the tip section 2 having fluid infusion and irrigation means 11. The fluid flow rate from the fluid infusion mechanism 11 may be between approximately 5 ml/min to 20 ml/min. In another embodiment, the tip section 2 of the catheter shaft 1 comprises a ball electrode 14 and at least one tip electrode 15 or band electrode 16. The electrodes are formed of conducting materials selected from the group of platinum, iridium, gold, silver, stainless steel, and Nitinol.

In order to enhance the ablation positioning of said ablation catheter, the electrode is encoded with at least one marker 17 which is visible to ultrasonic energy. Such marker 17 is provided in the form of encapsulated air bubbles. At least one marker 17 is placed in the proximity of the electrode 14 in a way so that the exact location of the tip section 2 is visible to an external ultrasonic energy. By way of example, the bubble in a marker can be formed by introducing air by a syringe (not shown) penetrating the wall of the substrate shaft of said catheter shaft and thereafter is sealed by epoxy.

The catheter system comprises a flat wire 18 which is disposed inside the lumen of the catheter shaft 1. The proximal end of said flat wire is secured to a deployment means 6 on the handle 4 of said catheter system, and is further connected to a conducting wire which is soldered to a contact pin of the connector 3. The at least one electrode 15 or 16 has an insulated conducting wire 19 secured to the electrode, which passes through the lumen of the catheter shaft 1 and is soldered to a contact pin of the connector 3 at the proximal end of the handle 4. The conducting wire from the connector end is externally connected to an EKG for diagnosis or to an RF generator during an electrophysiology ablation procedure. Therefrom, the RF energy is transmitted through the conducting wire to the electrode and delivered the energy to the target tissue.

A temperature sensor 20, either a thermocouple means or a thermister means, is constructed at the proximity of the electrode 14, 15, or 16 to measure the tissue contact temperature when RF energy is delivered. The temperature sensing wire 21 from the thermocouple or thermister is connected to one of the contact pins (not shown) of the connector 3 and externally connected to a transducer and to a temperature controller. The temperature reading is thereafter relayed to a close-loop control mechanism to adjust the RF energy output. The RF energy delivered is thus controlled by the temperature sensor reading or by a preprogrammed control algorithm.

Figure 4:
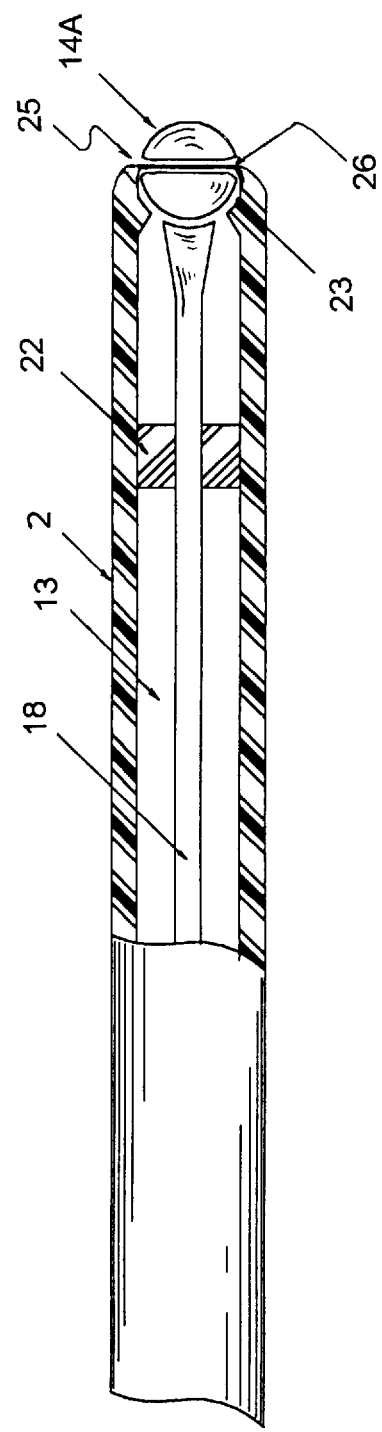
FIG. 4 is a close-up view of the distal section of an alternate catheter system comprising a ball electrode at the distal end having fluid infusion and irrigation capabilities.

FIG. 4 shows a close-up view of the distal section of an alternate catheter system comprising a ball electrode at the distal end having fluid infusion and irrigation capabilities. In one embodiment, the ball electrode 14A has two side holes and is suspended by the two support ears which are extended from the tip 7 of the catheter shaft 1. In another embodiment, a through hole 25 is created for the ball 14A. A shaft 26 which is secured at both sides to the tip 7 of the catheter shaft, passes through the through hole 25. In either case, the support ear and the shaft are made of conducting material and are connected to their respective conducting wires which are externally connected to an EKG for diagnosis or to an RF generator during an electrophysiology ablation procedure. Therefrom, the RF energy is transmitted through the conducting wire to the electrode and delivered the energy to the target tissue.

The catheter of this invention is also to provide fluid communication and commensurate flow of fluid originating inside the tip section of the catheter shaft to the electrode exterior surface, which directs the fluid flow from inside the catheter shaft over the exterior surface of the electrode to provide a fluid protective layer surrounding the electrode to minimize temperature elevation of the electrode with biological tissues. This fluid protective layer surrounding the ball electrode is better maintained when the ball of the ball electrode is freely rotatable.

To prevent blood or body fluid from backflow into the proximal end of the fluid conveying duct 13, a silicone type check valve 22 is installed at certain opening of the lumen of the fluid conveying duct 13. The fluid conveying duct 13 is further extended all the way to the hollow pocket 23 where a ball electrode 14 is disposed on the distal tip section 2 of the catheter shaft 1 and has an opening 24 facing the outside of the catheter shaft.

From the foregoing, it should now be appreciated that an improved catheter system having a ball electrode and a fluid infusion and irrigation capability has been disclosed for ablation procedures, including endocardial, epicardial, or body tissue and drug delivery operations for tumor or cancer management. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A method for operating a catheter system having a distal tip section with a ball electrode inside a hollow pocket, within a heart chamber, comprising:
   (a) percutaneously introducing the catheter system through a blood vessel to the heart chamber, wherein the distal tip section comprises a ball electrode;
   (b) deflecting the distal tip section of the catheter shaft about a transverse axis to position the electrode near a target on an interior wall of the heart chamber;
   (c) intimately contacting the electrode with the intracardiac tissue; and
   (d) applying RF energy to the ball electrode for ablation.

2. The method for operating an ablation catheter as in claim 1, further comprising fluid being supplied to the distal tip section of the catheter shaft and disposed out of the hollow pocket having a ball electrode.

3. The method for operating an ablation catheter as in claim 1, further comprising a steering mechanism at the handle for controlling the deflection of the distal tip section of said catheter system.

4. A catheter system comprising:
   a catheter shaft having a distal tip section, a distal end, a proximal end, and at least one lumen extending therebetween, wherein the distal tip section has a hollow pocket;
   a handle attached to the proximal end of the catheter shaft; and
   a ball disposed inside the pocket, wherein the ball is free to float, roll, or rotate within the pocket.

5. The catheter system as in claim 4, further comprising a conducting wire disposed inside the lumen, wherein the said conducting wire is to contact the ball.

6. The catheter system as in claim 5, further comprising fluid being supplied to the distal tip section of the catheter shaft and disposed out of the hollow pocket having a ball electrode.

7. The catheter system as in claim 6, further comprising fluid being selected from the group of saline, heparin, antibiotics, chemotherapy and therapeutic fluids.

8. The catheter system as in claim 7, wherein the fluid is supplied by a controlling means for controlling the flow rate of fluid through the lumen to optimize the cooling of the electrode of the catheter.

9. The catheter system as in claim 8, further comprising at least one ultrasonic visible marker being disposed at the distal tip section.

10. The catheter system as in claim 5, further comprising RF energy is delivered to said ball electrode disposed at the distal tip section.

11. The catheter system as in claim 10, further comprising at least one temperature sensing means at the distal tip section, and a close-loop temperature control mechanism for the catheter system.

12. The catheter system as in claim 5, further comprising at least one additional electrode disposed at the distal tip section of said catheter shaft.

13. The ablation catheter as in claim 12, further comprising the material of the electrode being selected from the group of platinum, iridium, gold, silver, stainless steel, and Nitinol.

14. The catheter system as in claim 5, further comprising the ball electrode being disposed at the distal end of the catheter shaft.

15. The catheter system as in claim 5, further comprising the ball electrode being disposed at the side of the distal tip section of the catheter shaft.

16. The catheter system as in claim 4, further comprising a steering mechanism at the handle for controlling the deflection of the distal tip section of said catheter system.

17. The catheter system as in claim 16, further comprising a steering mechanism at the handle, wherein said steering mechanism provides a plurality of deflectable curves on the distal tip section of the catheter system.

18. A tissue ablation catheter system comprising:
   a catheter shaft having a distal tip section, a distal end, a proximal end, and at least one lumen extending therebetween, wherein the distal tip section has a hollow pocket;
   a handle attached to the proximal end of the catheter shaft; and
   a ball electrode disposed inside the pocket, wherein the ball is free to float, roll, or rotate within the pocket.

19. The tissue ablation catheter system as in claim 18, further comprising a RF energy generating means, wherein the RE energy is applied to the ball electrode disposed at the distal tip section.

20. The tissue ablation application as in claim 19, further comprising fluid being supplied to the distal tip section of the catheter shaft and disposed out of the hollow pocket having a ball electrode.

* * * * *